US006967003B2

(12) United States Patent
Takehisa et al.

(10) Patent No.: US 6,967,003 B2
(45) Date of Patent: Nov. 22, 2005

(54) ARTIFICIAL LUNG OF MEMBRANE TYPE

(75) Inventors: Toru Takehisa, Chiba (JP); Kazunari Sakai, Chiba (JP); Susumu Kashiwabara, Shiga (JP); Hidenori Tanaka, Shiga (JP); Masaki Satoh, Shiga (JP); Hisateru Takano, Osaka (JP); Yoshiyuki Taenaka, Osaka (JP); Eisuke Tatsumi, Osaka (JP); Tomohiro Nishinaka, Osaka (JP)

(73) Assignees: Dainippon Ink and Chemicals, Inc., Tokyo (JP); Toyo Boseki Kabushiki Kaisha, Osaka (JP)

( * ) Notice: Subject to any disclaimer, the term of this patent is extended or adjusted under 35 U.S.C. 154(b) by 308 days.

(21) Appl. No.: 09/964,894

(22) Filed: Sep. 28, 2001

(65) Prior Publication Data

US 2003/0064003 A1    Apr. 3, 2003

(51) Int. Cl.[7] .................. A61M 37/00; A61M 1/14; B01D 63/00
(52) U.S. Cl. .................. 422/45; 422/44; 604/6.14; 210/321.62; 261/DIG. 28
(58) Field of Search .................. 422/45–48, 44; 604/265, 266, 4.01, 5.01, 6.14; 424/424; 510/384; 514/56, 822; 623/23.64, 23.65; 210/321.6, 321.61, 321.62, 321.87–321.89, 210/322, 323.1–323.2; 96/243, 267; 261/1–3, 261/19, 20, 24–5, 30, 75, 100, DIG. 28; 95/149, 95/155, 291; 138/88, 89, 93, 87.01

(56) References Cited

U.S. PATENT DOCUMENTS

| | | | |
|---|---|---|---|
| 3,844,989 A | * | 10/1974 | Harumiya et al. .......... 523/112 |
| 4,225,498 A | * | 9/1980 | Baudouin et al. .......... 548/435 |
| 4,349,467 A | * | 9/1982 | Williams et al. .......... 525/54.2 |
| 5,013,717 A | * | 5/1991 | Solomon et al. .......... 514/56 |
| 5,047,020 A | * | 9/1991 | Hsu .......... 604/266 |
| 5,128,408 A | * | 7/1992 | Tanaka et al. .......... 525/54.2 |
| 5,192,320 A | * | 3/1993 | Anazawa et al. .......... 623/23.65 |
| 5,525,348 A | * | 6/1996 | Whitbourne et al. ....... 424/423 |

FOREIGN PATENT DOCUMENTS

| | | |
|---|---|---|
| EP | 0 219 053 A2 | 4/1987 |
| EP | 0 229 381 A | 1/1989 |
| EP | 0 769 503 A2 | 4/1997 |
| EP | 0 781 566 A2 | 7/1997 |
| EP | 1 057 492 A1 | 12/2000 |
| EP | 1 120 123 A | 8/2001 |

OTHER PUBLICATIONS

Patent Abstracts of Japan, vol. 1998, No. 11, Sep. 30, 1998 & JP 10 152579 A (Toyobo Co. Ltd.), Jun. 9, 1998 *abstract*.
Patent Abstracts of Japan, vol. 1998, No. 11, Sep. 30, 1998 & JP 155898 A (Toyobo Co. Ltd.), Jun. 16, 1998 *abstract*.
Database WPI, Section Ch, Week 199307, Derwent Publications Ltd., London, GB; AN 1993-054822 XP002121868 & JP 05 003916 A (Nippon Koden Corp.), Jan. 14, 1993 *abstract*.
Database WPI, Section Ch, Week 199304, Derwent Publications Ltd., London, GB; AN 1999-038645 XP002121869 & JP 10 295800 A (Toyobo KK.), Nov. 10, 1998 *abstract*.
Database WPI, Section Ch, Week 199935, Derwent Publications Ltd., London, GB; AN 1999-411994 XP002121870 & JP 11 164882 A (Toyobo KK.), Jun. 22, 1999 *abstract*.

* cited by examiner

Primary Examiner—Patricia Bianco
(74) Attorney, Agent, or Firm—Armstrong, Kratz, Quintos, Hanson & Brooks, LLP

(57) ABSTRACT

A membrane artificial lung performs gas exchange between blood and a gas via the membrane by flowing the blood in one side of the membrane and flowing oxygen or an oxygen-containing gas in the other side of the membrane. The membrane has a hollow fiber membrane of poly-4-methyl-pentene-1 and an oxygen permeation rate $Q(O_2)$ at 25° C. of from $1\times10^{-6}$ to $3\times10^{-3}$ $(cm^3(STP)/cm^2 \cdot sec \cdot cmHg)$ and an ethanol flux of from 0.1 to 100 $ml/min \cdot m^2$. The membrane has, in the side of the blood flow, a surface having an ionic complex derived from: quaternary aliphatic alkylammonium salts; and heparin or a heparin derivative. The quaternary alkylammonium salts are a quaternary aliphatic alkylammonium salt having from 22 to 26 carbon atoms in total and a quaternary aliphatic alkylammonium salt having from 37 to 40 carbon atoms in total.

4 Claims, No Drawings

ARTIFICIAL LUNG OF MEMBRANE TYPE

FIELD OF THE INVENTION

This invention relates to an artificial lung of membrane type. More particularly, it relates to an artificial lung of membrane type which suffers from no plasma leakage and has excellent antithrombotic properties.

BACKGROUND OF THE INVENTION

Studies have been made on artificial lungs as supporting means in open-heart surgery or supporting means of respiration over a long period of time. Thus, there have been developed artificial lungs of various types. It is generally needed to impart antithrombotic properties to these artificial lungs so as to prevent blood coagulation.

To impart the antithrombotic properties, for example, U.S. Pat. No. 6,200,588 discloses a method of improving the antithrombotic properties by coating the surface of a part of a medical instrument to be contacted with blood with an ionic complex derived from: a quaternary alkylammonium salt having from 24 to 32 carbon atoms in total; and heparin or a heparin derivative. However, if the method disclosed therein is applied to the production of an artificial lung, there arises a problem that the artificial lung thus obtained frequently suffers from thrombus formation when used for a long time.

It is generally required that artificial lungs have characteristics such as not undergoing so-called wet lung (i.e., a phenomenon wherein vapor condenses and spreads out over the membrane surface in the side to be contacted with blood, thereby lessening the gas exchange area) and not hematologically activating complements. However, polyurethane, polyvinyl chloride and polycarbonate disclosed by U.S. Pat. No. 6,200,588 as medical instrument bases are insufficient in the above-described characteristics. Thus, the medical instruments disclosed by U.S. Pat. No. 6,200,588 are insufficient in the above-described characteristics as artificial lungs.

SUMMARY OF THE INVENTION

Accordingly, an object of the invention is to provide an artificial lung which suffers from no thrombus formation when used for a long time.

Another object of the invention is to provide an artificial lung which scarcely undergoes wet lung and is highly biocompatible (for example, scarcely activating complements hematologically).

Other objects and effects of the present invention will become apparent from the following description.

The inventors conducted extensive studies to achieve the above-described objects and consequently found out that antithrombotic properties can be improved by coating the surface of an artificial lung with an ionic complex derived from: two kinds of quaternary aliphatic alkylammonium salts, which differ from each other in alkyl chain length; and heparin or a heparin derivative.

The inventors further found out that the wet lung phenomenon and the hematological activation of complements can be inhibited by using, as the membrane of an artificial lung, a hollow fiber membrane which is made of poly-4-methylpentene-1 and has an oxygen permeation rate $Q(O_2)$ at 25° C. of from $1\times10^{-6}$ to $3\times10^{-3}$ ($cm^3(STP)/cm^2 \cdot sec \cdot cmHg$) and an ethanol flux of from 0.1 to 100 $ml/min \cdot m^2$.

The invention has been completed based on these technical findings. That is, the invention provides the following membrane artificial lung.

1) A membrane artificial lung for performing gas exchange between blood and a gas via the membrane by flowing the blood in one side of the membrane and flowing oxygen or an oxygen-containing gas in the other side of the membrane, wherein said membrane comprises a hollow fiber membrane, said hollow fiber membrane comprising poly-4-methylpentene-1 and having an oxygen permeation rate $Q(O_2)$ at 25° C. of from $1\times10^{-6}$ to $3\times10^{-3}$ ($cm^3(STP)/cm^2 \cdot sec \cdot cmHg$) and an ethanol flux of from 0.1 to 100 $ml/min \cdot m^2$, wherein said membrane has, in the side of the blood flow, a surface comprising an ionic complex derived from:
quaternary aliphatic alkylammonium salts; and
heparin or a heparin derivative, and
wherein said quaternary alkylammonium salts comprise at quaternary aliphatic alkylammonium salt having from 22 to 26 carbon atoms in total and a quaternary aliphatic alkylammonium salt having from 37 to 40 carbon atoms in total.

2) The membrane artificial lung according to item 1) above, wherein said quaternary alkylammonium salt comprises from 5 to 35% by weight of a quaternary aliphatic alkylammonium salt having from 22 to 26 carbon atoms in total and from 65 to 95% by weight of a quaternary aliphatic alkylammonium salt having from 37 to 40 carbon atoms in total.

3) The membrane artificial lung according to item 1) or 2) above, wherein said quaternary aliphatic alkylammonium salt comprise a dimethyldidodecylammonium salt and a dimethyldioctadecylammonium salt.

DETAILED DESCRIPTION OF THE INVENTION

The membrane to be used in the artificial lung of membrane type according to the invention is made of poly-4-methylpentene-1. This membrane has an oxygen permeation rate $Q(O_2)$ ranging from $1\times10^{-6}$ to $3\times10^{-3}$ ($cm^3(STP)/cm^2 \cdot sec \cdot cmHg$), preferably from $1\times10^{-5}$ to $3\times10^{-3}$ ($cm^3(STP)/cm^2 \cdot sec \cdot cmHg$) and still preferably from $5\times10^{-4}$ to $2\times10^{-3}$ ($cm^3(STP)/cm^2 \cdot sec \cdot cmHg$) (the oxygen permeation rate is measured in accordance with ASTM D1434).

In case where the oxygen permeation rate is less than the lower limit as defined above, the artificial lung is clinically unusable because of the insufficient capability of eliminating carbon dioxide. In case where the oxygen permeation rate exceeds the upper limit as defined above, the artificial lung is unusable because of the serious plasma leakage. Since the carbon dioxide permeation rate of the membrane to be used in the invention is almost comparable or higher than the oxygen permeation rate, the membrane having such oxygen permeation rate as defined above has a sufficient capability of eliminating carbon dioxide from the blood. As a matter of course, a higher oxygen permeation rate is the more favorable from the viewpoint of the gas exchange performance. The oxygen permeation rate can be elevated by, for example, selecting a material having a large oxygen permeation rate coefficient, elevating the porosity, or reducing the substantial membrane thickness through which a gas permeates with the dissolution/diffusion mechanism of the polymer in the membrane material. However it is unfavorable that the oxygen permeation rate exceeds the upper limit as defined above, since the pore size and porosity of the membrane are considerably enlarged and thus plasma leakage frequently arises in case where the pores are in the open-cell structure.

In the hollow fiber membrane to be used in the artificial lung of the invention, the ethanol flux is employed as an indication of the plasma leakage from the membrane. In case where the membrane has pores in the open-cell structure, ethanol enters therein and permeates through the membrane as a liquid. At a larger ethanol flux, plasma leakage arises the more frequently. The hollow fiber membrane to be used in the artificial lung of the invention preferably has an ethanol flux of 100 ml/(min·m$^2$) or less, still preferably 60 ml/(min·m$^2$) or less and particularly, preferably 10 ml/(min·m$^2$) or less. It is unfavorable that the ethanol flux exceeds the above-described level, since the membrane suffers from serious plasma leakage in this case. It is also unfavorable that the ethanol flux is less than 0.1 ml/(min·m$^2$), since the gas exchange efficiency of the membrane is worsened in this case. Thus, it is preferable that the ethanol flux is at least 0.1 ml/(min·m$^2$).

It is also preferable that the membrane made of poly-4-methylpentene-1 to be used in the artificial lung according to the invention has a melt index (MI) (as defined in accordance with ASTM D1238) of from 5 to 50 (g/10 min), still preferably from 20 to 32 (g/10 min). In case where the MFR is less than 5 (g/10 min), the membrane has only an insufficient strength. In case where the MI exceeds 50 (g/10 min), it is impossible to produce a uniform membrane. That is to say, membranes having MIs higher than the upper limit or less than the lower limit each as defined above are unusable because of the poor structural stability.

The poly-4-methylpentene-1 constituting the membrane to be used in the invention is characterized by being a material with large permeation coefficients with respect to oxygen and carbon dioxide, being highly compatible with blood, allowing to easily control the pore size arbitrarily, allowing the formation of a membrane by the melt method free from any fear of residual solvents, enabling the formation of a thin membrane owing to the high mechanical strength and thus allowing the construction of a compact apparatus, being contaminated with little harmful impurities, being easily handled because of having no water absorption property, being easily sterilized because of having high chemical resistance, and being less expensive.

Because of having the smallest surface energy among polyolefin polymers, furthermore, poly-4-methylpentene-1 scarcely undergoes so-called wet lung (i.e., a phenomenon wherein vapor condenses and spreads out over the membrane surface in the side to be contacted with blood, thereby lessening the gas exchange area) and hardly activates complements hematologically, which makes it particularly suitable as a material of artificial lungs of membrane type usable over a long time.

The material comprising poly-4-methylpentene-1 to be used in the invention may contain other components, so long as it has poly-4-methylpentene-1 as the main component. For example, it may contain crosslinking agents, antibacterial agents and the like or it may be blended with other polymers.

The membrane to be used in the artificial lung of membrane type according to the invention has fine pores (voids) within the membrane. Now, the pore structure will be illustrated in detail. Pores with a relatively large size are provided in one side of the membrane (i.e., the outer or inner surface of the hollow fiber membrane). On the other hand, the other side of the membrane has, for example, the following structure (1), (2) or (3).

(1) No pore is opened, or pores provided with a very fine layer of blocking plasma leakage are formed.

(2) Pores having a relatively large size are formed within the membrane but these pores are not opened on both of the outer and inner surfaces of the membrane, or pores provided with a very fine layer of blocking plasma leakage are formed.

(3) No pore is opened on both of the outer and inner surfaces of the membrane, or pores are not bored through the membrane but ended halfway, or pores provided with a very fine layer of blocking plasma leakage are formed.

In practice, these structures (1) to (3) are mixed together in many cases. Due to the above-described structure, the membrane to be used in the artificial lung of membrane type according to the invention has irregular pore sizes. The pore size and the pore size distribution in the membrane are not particularly restricted, so long as they are controlled so as to achieve the oxygen permeation rate and ethanol flux as defined above. Among all, it is preferable that the pore size ranges from 0.005 to 10 μm, still preferably from 0.03 to 1 μm. A part wherein pores are not bored through the membrane and a part wherein pores provided with a very fine layer of blocking plasma leakage are formed may be obtained by employing the melt molding method disclosed by JP-B-7-12134 or the heat-induced phase separation method disclosed by JP-A-62-106770 (the term "JP-B" as used herein means an "examined Japanese patent publication", while the term "JP-A" as used herein means an "unexamined published Japanese patent application"). Alternatively, use may be also made of means of forming a thin film on a membrane of the open-cell structure by coating, etc. as disclosed by JP-A-62-64373, JP-A-60-249968 and JP-A-61-31164.

The artificial lung of membrane type according to the invention is characterized in that a hollow fiber membrane having characteristic permeation properties is used as a gas exchange membrane of the artificial lung. Although it may have an arbitrary structure of external perfusion type, internal perfusion type, etc., it is favorable to employ the external perfusion structure from the viewpoints of achieving high gas exchange efficiency and minimizing blood damage. An artificial lung of the external perfusion type may be constructed by, for example, forming a cord-fabric sheet of the hollow fiber membrane and integrating it into the artificial lung to thereby prevent blood channeling (i.e., short-pass of blood without gas exchange). Thus, improved membrane performance can be established.

In case of using in internal perfusion, the artificial lung of membrane type according to the invention may be in the form of for example, a cylinder which comprises a hollow fiber membrane having a total area of the hollow fiber inside of from 0.1 to 7 m$^2$ and containing from 1,000 to 100,000 hollow fiber yarns and has a gas exchange area of about 25 cm or less in outer diameter and 30 cm or less in height.

In case of using in external perfusion, on the other hand, the artificial lung of membrane type according to the invention may be in the form of, for example, a cylinder or a rectangular parallelepiped which comprises a hollow fiber membrane having a total area of the hollow fiber outside of from 0.1 to 3.5 m$^2$ and containing from 1,000 to 60,000 hollow fiber yarns and has a gas exchange area of about 20 cm or less in outer diameter and 30 cm or less in height (in case of a cylinder) or 20 cm or less in each edge (in case of a rectangular parallelepiped).

It is preferable that the membrane to be used in the artificial lung of membrane type according to the invention is in the form of a cord fabric-type sheet of hollow fiber. As such a cord fabric-type sheet, use can be made of, for example, a sheet obtained by weaving the warp vertically to the hollow fiber, or weaving the hollow fiber with the use of a pressure-sensitive adhesive tape, or bonding the hollow fiber with the use a thread carrying an adhesive, though the invention is not restricted thereto.

It is generally adequate to produce the membrane to be used in the artificial lung of membrane type according to the invention by the melt method, the dry method or the dry-wet method, though the invention is not restricted thereto. Among all, it is particularly adequate to employ the melt method from the viewpoints of the membrane performance and productivity. Namely, the membrane can be produced by the methods disclosed by JP-A-59-196706; JP-A-59-229320, JP-A-61-101206, JP-A-61-101227 and the like. To impart to the hollow fiber membrane favorable abilities to supply oxygen to the blood, to prevent plasma leakage and to withstand utilization over a long time without causing any deterioration in the performance, it is preferable that the production by the melt molding method is carried out under the following conditions.

Namely, the production is effected while controlling the melting temperature to from (Tm+15) to (Tm+65)° C. (wherein Tm stands for the melting point of the polymer crystal), the draw ratio (DR) in the amorphous drawing to from 1.0 to 1.1, the heating temperature to from (Tm−35) to (Tm−10)° C., the heating time to from 2 to 30 seconds, the DR to from 1.0 to 1.2, the DR in the cold drawing to from 1.1 to 1.6, and the DR in the hot drawing to from 1.3 to 2.0. By controlling these factors in respective steps each within the range as defined above, the oxygen permeation rate, porosity, blocking layer thickness, etc. can be arbitrarily designed to satisfy the requirements for the use as an artificial lung.

It is also possible to produce a porous membrane having a smooth blocking layer at least in one side of the hollow fiber membrane by extrusion-molding a molten polyolefin polymer, which has an ultimate degree of crystallization of 20% or more, into hollow fiber, then subjecting the fiber to orientation drawing and heating if needed, and then to cold drawing and heat fixation. Since a membrane produced by this method has pores which are longer in the vertical direction to the membrane surface due to the formation mechanism, it is characterized by showing a sufficiently high oxygen permeation rate and substantially no alcohol-permeability at a relatively low porosity, having an excellent mechanical strength, allowing considerable reduction in membrane thickness, being free from the elution of any toxic matters because of using no solvent, achieving a high productivity and thus enabling the membrane production at a much lower cost compared with complex membranes, etc.

The material to be used in the invention for imparting antithrombotic properties to the surface over a long time has the following constitution.

As a coating, use is made of a blood-compatible composition containing an ionic complex derived from aliphatic alkylammonium salts having 4 aliphatic alkyl groups attached thereto and heparin or a heparin derivative. In this blood-compatible composition, the above-described ammonium salts comprise from 5 to 65% by weight, based on the total ammonium salts, of an ammonium salt having from 22 to 26 carbon atoms, in total, in the 4 aliphatic alkyl groups.

As the ammonium salt having from 22 to 26 carbon atoms in total in the alkyl groups, dialkyldimethylammonium salts are preferable. Examples of the ammonium salt having from 22 to 26 carbon atoms in total in the alkyl groups include didecyldimethylammonium salts and dimethyldidodecylammonium salts. Among all, dimethyldidodecylammonium salts such as dimethyldidodecylammonium chloride and dimethyldidodecylammonium bromide are particularly preferable.

The content of the ammonium salt having from 37 to 40 carbon atoms in total in the alkyl groups is preferably from 35 to 95% by weight based on the total weight of the ammonium salts. If the content is lower than the above range, sufficient durability cannot be attained. On the other hand, if the content is higher than the above range, the hydrophobicity is excessively enhanced so that sufficient antithrombogenicity cannot be attained.

As the ammonium salt having from 37 to 40 carbon atoms in total in the alkyl groups, trialkylmethylammonium salts, dialkyldimethylammonium salts and dialkyldiethylammonium salts are preferable. Examples of the trialkylmethylammonium salts include tridodecylmethylammonium salts. Examples of the dialkyldimethylammonium salts include dimethyldioctadecylammonium salts. Examples of the dialkyldiethylammonium salts include diethyldioctadecyammonium salts. Among all, dimethyldioctadecylammonium salts such as dimethyldioctadecylammonium chloride and dimethyldioctadecylammonium bromide are particularly preferable.

In the artificial lung of membrane type according to the invention, an ionic complex of heparin with ammonium salts wherein plural ammonium salts differing from each other in the total carbon atom number in the four alkyl groups are used together with heparin. Thus, the most adequate antithrombotic properties, which cannot be obtained by using an ionic complex of an ammonium salt of a single structure with heparin, can be imparted. Particularly, the present invention is based on the finding that the use of a highly hydrophobic ammonium salt having a total carbon number of from 37 to 40 makes it possible to attain high affinity with respect to the hollow fiber made of poly-4-methylpentene-1, thereby providing optimum performances.

Examples of the heparin derivative include heparin sodium, heparin potassium, heparin lithium, heparin calcium, low-molecular weight heparin and epoxidized heparin.

The surface of the hollow fiber membrane constituting the artificial lung of membrane type according to the invention may be treated by, for example, the following method.

The ionic complex of the above-described mixture of ammonium salts each having 4 aliphatic groups attached thereto with heparin is mixed by stirring in a solvent to give a precipitate. Then this precipitate is collected and washed to thereby eliminate the unreacted heparin and organic cation compounds. Thus an ionic complex of heparin-ammonium salts each having 4 aliphatic groups attached thereto is obtained. Next, this ionic complex of heparin-ammonium salts each having 4 aliphatic groups attached thereto is dissolved in an organic solvent to give a coating agent comprising the ionic complex of heparin-organic cation and the organic solvent. Subsequently, this coating agent is brought into contact with the surface of the above-described hollow fiber membrane and then the organic solvent is eliminated. Thus an optimized antithrombotic surface can be formed on the surface of the hollow fiber membrane.

The coating agent comprising the ionic complex of heparin-ammonium salts each having 4 aliphatic groups attached thereto with the organic solvent is not restricted in concentration, so long as a film of the ionic complex of heparin-ammonium salts each having 4 aliphatic groups attached thereto can be formed on the surface of the above-described hollow fiber membrane. In usual, the concentration ranges from 0.01 to 5% by weight. From the viewpoint of forming a uniform coating film on the surface of the hollow fiber membrane, it is favorable that the concentration falls within the range of from 0.05 to 1.0% by weight.

As the organic solvent (I) in which the ionic complex of heparin-ammonium salts each having 4 aliphatic groups attached thereto is to be dissolved use may be made of, for example, n-hexane, cyclohexane, tetrahydrofuran (hereinafter referred to simply as THF), 1,4-dioxane, cyclohexanone, N,N-dimethylformamide, N,N-dimethylacetamide or N-methylpyrrolidone.

In addition to the organic solvents as described above, it is preferable that the organic solvent to be used in the coating agent comprising the ionic complex of heparin-ammonium salts each having 4 aliphatic groups attached thereto and the organic solvent can minimize the damage on the artificial lung membrane i.e., the base), the casing and the potting part for sealing the membrane. Examples of such an organic solvent (II) include methanol, ethanol, isopropyl alcohol and n-propyl alcohol.

Among the solvents as cited above, it is particularly preferable, from the viewpoint of not affecting the gas permeability of poly-4-methylpentene-1, to use a solvent mixture of ethanol with methanol, THF or cyclohexanone. It still preferable to use a solvent mixture of ethanol with THF from the viewpoint of the safety of the solvent.

The organic solvent (I) as described above may be used either alone or as a mixture thereof. Similarly, the above-described organic solvent (II) may be used either alone or as a mixture thereof.

The ionic complex of heparin-ammonium salts each having 4 aliphatic groups attached thereto may be contacted with the surface of the hollow fiber membrane by any other methods without restriction. For example, use can be made therefor of the immersion method, the spraying method, the brushing method or a method which comprises preliminarily dissolving an ammonium salt mixture in an adequate solvent, bringing into contact with the surface of a medical instrument, eliminating the organic solvent by drying, and then bringing into contact with an aqueous heparin solution to thereby form an ionic complex of heparin-ammonium salts each having 4 aliphatic groups attached thereto on the surface of the hollow fiber membrane.

EXAMPLES

The present invention will be illustrated in greater detail with reference to the following Examples, but the invention should not be construed as being limited thereto. In the following Examples, all the "parts" are given by weight unless otherwise indicated.

Synthesis Example 1

6 parts of didodecyldimethylammonium bromide manufactured by Tokyo Kasei Kogyo) and 14 parts of dimethyldioctadecylammonium bromide (manufactured by Polyscience, Inc.) were dissolved in 100 parts of methanol. To a solution of 10 parts of heparin dissolved in 100 parts of deionized water, the methanol solution containing the ammonium salts dissolved therein was dropped under stirring. Immediately after the dropping, a white precipitate was formed. After the completion of the dropping, the white precipitate was separated by filtration. After eliminating the unreacted heparin and ammonium salts from the precipitate by repeatedly washing with a solvent mixture of water and methanol several times, the residue was freeze-dried to give a white powder of a complex of heparin with the ammonium salts. This white powder was dissolved in a solvent mixture of ethanol and THF (80/20) to give a concentration of 0.1%. Thus, a solution (I) of the complex of heparin with the above-described ammonium salts (hereinafter referred to as "solution (I)") was obtained.

Synthesis Example 2

6 parts of didodecyldimethylammonium bromide (manufactured by Tokyo Kasei Kogyo) and 20 parts of diethyldioctadecylammonium bromide (manufactured by Tokyo Kasei Kogyo) were dissolved in 100 parts of methanol. To a solution of 10 parts of heparin dissolved in 100 parts of deionized water, the methanol solution containing the ammonium salts dissolved therein was dropped under stirring. Then a white powder of an ionic complex of heparin with the ammonium salts was obtained in the same manner as in Synthesis Example 1. This white powder was dissolved in a solvent mixture of ethanol and THF (80/20) to give a concentration of 0.1%. Thus, a solution (II) of the complex of heparin with the above-described ammonium salts (hereinafter referred to as "solution (II)") was obtained.

Synthesis Example 3

6 parts of didecyldimethylammonium chloride (manufactured by Tokyo Kasei Kogyo) and 14 parts of tridecylmethylammonium chloride (manufactured by ALDRICH) were dissolved in 100 parts of methanol. To a solution of 10 parts of heparin dissolved in 100 parts of deionized water, the methanol solution containing the ammonium salts dissolved therein was dropped under stirring. Then a white powder of an ionic complex of heparin with the ammonium salts was obtained in the same manner as in Synthesis Example 1. This white powder was dissolved in a solvent mixture of ethanol and THF (80/20) to give a concentration of 0.1%. Thus, a solution (III) of the complex of heparin with the above-described ammonium salts (hereinafter referred to as "solution (III)") was obtained.

Synthesis Example 4

6 parts of didodecyldimethylammonium bromide (manufactured by Tokyo Kasei Kogyo) and 13 parts of dihexadecyldimethylammonium bromide (manufactured by Tokyo Kasei Kogyo) were dissolved in 100 parts of methanol. To a solution of 10 parts of heparin dissolved in 100 parts of deionized water, the methanol solution containing the ammonium salts dissolved therein was dropped under stirring. Then a white powder of an ionic complex of heparin with the ammonium salts was obtained in the same manner as in Synthesis Example 1. This white powder was dissolved in a solvent mixture of ethanol and THF (80/20) to give a concentration of 0.1%. Thus, a solution (IV) of the complex of heparin with the above-described ammonium salts (hereinafter referred to as "solution (IV)") was obtained.

Synthesis Example 5

6 parts of didodecyldimethylammonium bromide (manufactured by Tokyo Kasei Kogyo) and 19 parts of ditetradecyldimethylammonium bromide (manufactured by Tokyo Kasei Kogyo) were dissolved in 100 parts of methanol. To a solution of 13 parts of heparin dissolved in 100 parts of deionized water, the methanol solution containing the ammonium salts dissolved therein was dropped under stirring. Then a white powder of an ionic complex of heparin with the ammonium salts was obtained in the same manner as in Synthesis Example 1. This white powder was dissolved in a solvent mixture of ethanol and THF (80/20) to give a concentration of 0.1%. Thus, a solution (V) of the complex of heparin with the above-described ammonium salts (hereinafter referred to as "solution (V)") was obtained.

Synthesis Example 6

17 parts of didodecyldimethylammonium bromide (manufactured by Tokyo Kasei Kogyo), 58 parts of ditetradecyldimethylammonium bromide (manufactured by Tokyo Kasei Kogyo), and 60 parts of dihexadecyldimethylammonium bromide (manufactured by Tokyo Kasei Kogyo) were dissolved in 250 parts of methanol. To a solution of 50 parts of heparin dissolved in 180 parts of deionized water, the methanol solution containing the ammonium salts dissolved therein was dropped under stirring. Then a white powder of an ionic complex of heparin with the ammonium salts was obtained in the same manner as in Synthesis Example 1. This white powder was dissolved in a solvent mixture of ethanol and THF (80/20) to give a concentration of 0.1%. Thus, a solution (VI) of the complex of heparin with the above-described ammonium salts (hereinafter referred to as "solution (VI)") was obtained.

Production Example 1

Poly-4-methylpentene-1 having a melt index (determined according to ASTM D1238) of 26 was melt-spun by using a torus nozzle (diameter: 6 mm) for hollow fiber at a spinning temperature of 290° C., at a taking-off speed of 100 mm/min, and at a draft (the winding/extrusion speed ratio) of 270 to thereby give hollow fiber of 275 $\mu$m in outer diameter and 34 $\mu$m in membrane thickness. In this step, the hollow fiber located from 3 to 35 cm under the nozzle port was cooled with an air stream at a temperature of 25° C. at a flow rate of 1.5 m/sec. The hollow fiber thus obtained was continuously drawn in the amorphous state at a temperature of 35° C. at a draw ratio (DR) of 1.05 with the use of a roller system. Subsequently, it was heat-treated by introducing into a hot air-circulation type thermostat at 200° C. at a DR of 1.3 and pooling therein for 5 seconds. Next, it was subjected to cold drawing (35° C., DR 1.2), hot drawing (150° C., DR 1.2) and heat fixation (200° C., DR 0.9) to thereby give a hollow fiber membrane of 255 $\mu$m in outer diameter and 27 $\mu$m in membrane.

Then, an artificial lung of membrane type (hereinafter referred to as the artificial lung $A_0$) having a membrane area of 0.8 m$^2$ was constructed by using this hollow fiber membrane. The gas permeation rates of the hollow fiber part of this artificial lung of membrane type $A_0$ determined in accordance with the pressure method as defined in ASTM D1434 were as follows: $Q(O_2)=6\times10^{-4}$ cm$^3$(STP)/ (cm$^2$·sec·cmHg), $Q(CO_2)=5.5\times10^{-4}$ cm$^3$(STP)/ (cm$^2$·sec·cmHg).

In the hollow part side of the above-described artificial lung $A_0$ (effective membrane area: 0.8 m$^2$), a 70% aqueous solution of ethanol for moistening the membrane was flowed at a rate of 200 cm$^3$/min to give an intermembrane pressure difference of 0.5 kgf/cm$^2$. The 70% ethanol flux thus determined was 7.5 ml/(min·m$^2$). To examine the possibility of plasma leakage from the membrane, the blood contact side (i.e., the outer side of hollow fiber) of the membrane was perfused with physiological saline (37° C.) containing 5% of albumin and 0.15% of phospholipids and the albumin thus eluted was determined. As a result, not more than 10 mg/dl of albumin was leaked after perfusing at a flow rate of 2 L/min/m$^2$ under a perfusion pressure of 500 mmHg for 6 hours while maintaining the solution at a temperature of 37° C. The albumin leakage was determined by binding a dye to the leaked albumin (the pyrogallol red-molybdenum complex color development method) with the use of an albumin assay kit (Micro TP Test Wako™ manufactured by Wako Pure Chemical Industries).

Production Example 2

Poly-4-methylpentene-1 having a melt index (determined according to ASTM D1238, of 26 was melt-spun by using a torus nozzle (diameter: 6 mm) for hollow fiber at a spinning temperature of 290° C., at a taking-off speed of 60 m/min, and at a draft of 270 to thereby give hollow fiber of 275 $\mu$m in outer diameter and 34 $\mu$m in membrane thickness. In this step, the hollow fiber located from 3 to 35 cm under the nozzle port was cooled with an air stream at a temperature of 25° C. at a flow rate of 0.5 m/sec. The hollow fiber thus obtained was continuously drawn in the amorphous state at a temperature of 35° C. at a draw ratio (DR) of 1.05 with the use of a roller system. Subsequently, it was heat-treated by introducing into a hot air-circulation type thermostat at 200° C. at a DR of 1.03 and pooling therein for 5 seconds. Next, it was subjected to cold drawing (35° C., DR 1.3), hot drawing (150° C., DR 1.4) and heat fixation (200° C., DR 0.9) to thereby give a hollow fiber membrane of 255 $\mu$m in outer diameter and 27 $\mu$m in membrane.

Then, an artificial lung of membrane type (hereinafter referred to as the artificial lung $B_0$) having a membrane area of 0.8 m$^2$ was constructed by using this hollow fiber membrane. The gas permeation rates of the hollow fiber part of this artificial lung of membrane type $B_0$ determined in accordance with the pressure method as defined in ASTM D1434 were as follows: $Q(O_2)=2.0\times10^{-3}$ cm$^3$(STP)/ (cm$^2$·sec·cmHg), $Q(CO_2)=1.85\times10^{-3}$ cm$^3$(STP)/ (cm$^2$·sec·cmHg).

The 70% ethanol flux of the hollow part side of the above-described artificial lung $B_0$ (effective membrane area: 0.8 m$^2$) determined as in Production Example 1 was 60.0 cm$^3$/(min·m$^2$). To examine the possibility of plasma leakage from the membrane, the albumin elution was determined as in Production Example 1. As a result, not more than 10 mg/dl of albumin was leaked after perfusing at a flow rate of 2 L/min/m$^2$ under a perfusion pressure of 500 mmHg for 6 hours while maintaining the solution at a temperature of 37° C.

Production Example 3

Poly-4-methylpentene-1 having a melt index (determined according to ASTM D1238) of 26 was melt-spun by using a torus nozzle (diameter: 6 mm) or hollow fiber at a spinning temperature of 295° C., at a taking-off speed of 300 m/min, and at a draft of 270 to thereby give hollow fiber of 275 $\mu$m in outer diameter and 34 $\mu$m in membrane thickness. In this step, the hollow fiber located from 3 to 35 cm under the nozzle port was cooled with an air stream at a temperature of 25° C. at a flow rate of 1.5 m/sec. The hollow fiber thus obtained was continuously drawn in the amorphous state at a temperature of 35° C. at a draw ratio (DR) of 1.05 with the use of a roller system. Subsequently, it was heat treated by introducing into a hot air-circulation type thermostat at 200° C. at a DR of 1.3 and pooling therein for 5 seconds. Next, it was subjected to cold drawing (35° C., DR 1.2), hot drawing (150° C., DR 1.2) and heat fixation (200° C., DR 0.9) to thereby give a hollow fiber membrane of 255 μm in outer diameter and 27 μm in membrane.

Then, an artificial lung of membrane type (hereinafter referred to as the artificial lung $C_0$) having a membrane area of 0.8 m² was constructed by using this hollow fiber membrane. The gas permeation rates of the hollow fiber part of this artificial lung of membrane type $C_0$ determined in accordance with the pressure method as defined in ASTM D1434 were as follows: $Q(O_2)=4.5\times10^{-5}$ cm³(STP)/(cm²·sec·cmHg), $Q(CO_2)=3.4\times10^{-5}$ cm³(STP)/(cm²·sec·cmHg).

The 70% ethanol flux of the hollow part side of the above-described artificial lung $C_0$ (effective membrane area 0.8 m²) determined as in Production Example 1 was 0.8 cm³(min·m²). Thus, it was found out that this membrane had a very low ethanol flux. To examine the possibility of plasma leakage from the membrane, the albumin elution was determined as in Production Example 1. As a result, not more than 10 mg/dl of albumin was leaked after perfusing at a flow rate of 2 L/min/m² under a perfusion pressure of 500 mmHg for 6 hours while maintaining the solution at a temperature of 37° C.

Production Example 4

Using a porous polypropylene hollow fiber membrane of the open-cell type (outer diameter: 350 μm, membrane thickness: 40 μm), an artificial lung ($D_0$) having a membrane area of 0.8 m² was constructed. When determined as in Production Example 1, the hollow fiber part of this artificial lung of membrane type $D_0$ showed considerably high permeation rates, compared with the artificial lung $A_0$ constructed in Production Example 1, as follows: $Q(O_2)=3.7\times10^{-2}$ cm³(STP)/(cm²·sec·cmHg), $Q(CO_2)=3.4\times10^{-2}$ cm³(STP)/(cm²·sec·cmHg).

The 70% ethanol flux of the hollow part side of the above-described artificial lung $D_0$ as 239 cm³/(min·m²). Thus, it was found out that this artificial lung $D_0$ had a considerably higher ethanol flux than the artificial lung $A_0$. Then the above-described artificial lung $D_0$ was subjected to the test for examining the possibility of plasma leakage as in Production Example 1. As a result, 126 mg/dl and 227 mg/dl of albumin was leaked from the hollow fiber packed in the above-described artificial lung $D_0$ respectively 1 hour and 6 hours after the initiation of the experiment.

Example 1

The artificial lung ($A_0$) obtained in Production Example 1 was heated to 50° C. with a hot air stream. Then the solution (I) prepared in Synthesis Example 1 was heated to 50° C. and filled in the blood-contact face (i.e., the outer face of the hollow-fiber) of the artificial lung. After confirming that the blood-contact face of the artificial lung had been completely immersed in the solution (I), the filled solution (I) was discharged by applying nitrogen gas pressure to the solution. After discharging the solution (I), the above-described artificial lung was dried by blowing a nitrogen gas from both of the inside and outside of the artificial lung. Thus an artificial lung (A1) having a coating film of the solution (I) on the blood-contact face was constructed.

The hollow fiber membrane packed in the above-described artificial lung (A1) was taken out and the amount of heparin fixed on the membrane surface (the face provided with the coating film) was quantified. As a result, it could be confirmed that 30 mU/cm² of heparin had been fixed on the hollow fiber surface. The fixed heparin was quantified by the anti-Xa activity method (i.e., quantifying heparin based on the blood coagulation factor Xa inhibitory activity) with the use of a heparin assay kit (Testzyme Heparin™ manufactured by Daiichi Kagaku Yakuhin).

The blood-contact face (the outer face of the hollow fiber) of the above-described artificial lung (A1) was filled with 2 L of physiological saline and then perfused for 4 hours at a flow rate of 1 L/min at room temperature. Next, the artificial lung was thoroughly washed with distilled water and dried so as to completely eliminate the physiological saline from the perfused part. Then the above-described artificial lung was disintegrated and the hollow fiber packed therein was taken out. Subsequently, the heparin having been fixed on the hollow fiber surface was quantified by the above-described method. As a result, it could be confirmed that 26 mU/cm² of heparin had been fixed. Next, the above perfusion experiment was repeated but carrying out the perfusion with physiological saline for 24 hours and the heparin having been fixed on the hollow fiber surface was quantified. As a result, it could be confirmed that 24 mU/cm² of heparin had been fixed. Thus, it was confirmed that heparin was preserved on the hollow fiber surface even after the prolonged contact with sodium chloride contained in the physiological saline.

Next, a chronic animal experiment was performed to examine the efficacy of the artificial lung (A1). The animal employed was an adult goat weighing 44 kg. Under anesthesia, 44 mg of heparin (corresponding to 1 mg of heparin per kg of the body weight of the adult goat) was administered in order to prevent thrombus formation due to surgical operation. Subsequently, the right carotid and the right external jugular vein were exposed and a blood-supplying cannula and a blood-removing cannula were inserted respectively thereinto. Next, these cannulae were connected to a blood circuit for a percutaneous cardiopulmonary support (PCPS) involving the artificial lung (A1) of the invention integrated thereinto and perfusion was initiated at a blood circulation rate of 3 L/min. During the circulation period, no antithrombotic treatment (administration of heparin, etc.) was performed. Although the blood circulation with the PCPS was continued for 20 days, neither any decrease in the gas exchange capability of the artificial lung A1 nor any complication caused by thrombi (organ insufficiency, etc.) was observed during this period. After the completion of the experimental schedule over 20 days, the inside of the employed artificial lung (A1) was observed in detail. As a result, no large thrombus was formed therein, which indicated that favorable antithrombotic properties could be sustained.

Example 2

Using the artificial lung $B_0$ obtained in Production Example 2 and the solution (I) obtained in Synthesis Example 1, an artificial lung (B1) having a coating film of the above-described solution (I) on the blood-contact face of the above-described artificial lung $B_0$ was constructed as in Example 1. On the hollow fiber surface of this artificial lung (B1), 28 mU/cm² of heparin had been fixed. Then the blood-contact face (the outer face of the hollow fiber) of this artificial lung (B1) was filled with 2 L of physiological saline and perfused with the physiological saline for 4 hours and 24 hours followed by washing and drying as in Example 1. Thus, heparin having been fixed on the hollow fiber surface was quantified. As a result, it was confirmed that 25 mU/cm² and 22 mU/cm² of heparin had been fixed respectively after perfusing for 4 and 24 hours.

Example 3

Using the artificial lung $C_0$ obtained in Production Example 3 and the solution (I) obtained in Synthesis Example 1, an artificial lung (C1) having a coating film of the above-described solution (I) on the blood-contact face of the above-described artificial lung $C_0$ was constructed as in Example 1. On the hollow fiber surface of this artificial lung (C1), 28 mU/cm² of heparin had been fixed. Then the blood-contact face of this artificial lung (C1) was filled with 2 L of physiological saline and perfused with the physiological saline for 4 hours and 24 hours followed by washing and drying as in Example 1. Thus, heparin having been fixed on the hollow fiber surface was quantified. As a result, it was confirmed that 25 mU/cm² and 23 mU/cm² of heparin had been fixed respectively after perfusing for 4 and 24 hours.

Example 4

Using the artificial lung $A_0$ obtained in Production Example 1 and the solution (II) obtained in Synthesis Example 2, an artificial lung (A2) having a coating film of the above-described solution (II) on the blood-contact face of the above-described artificial lung $A_0$ was constructed as in Example 1. On the hollow fiber surface of this artificial lung (A2), 25 mU/cm² of heparin had been fixed. Then the blood-contact face of this artificial lung (A2) was filled with 2 L of physiological saline and perfused with the physiological saline for 4 hours and 24 hours followed by washing and drying as in Example 1. Thus, heparin having been fixed on the hollow fiber surface was quantified. As a result it was confirmed that 15 mU/cm² and 13 mU/cm² of heparin had been fixed respectively after perfusing for 4 and 24 hours.

Example 5

Using the artificial lung $A_0$ obtained in Production Example 1 and the solution (III) obtained in Synthesis Example 3, an artificial lung (A3) having a coating film of the above-described solution (III) on the blood-contact face of the above-described artificial lung $A_0$ was constructed as in Example 1. On the hollow fiber surface of this artificial lung (A3), 20 mU/cm² of heparin had been fixed. Then the blood-contact face of this artificial lung (A3) was filled with 2 L of physiological saline and perfused with the physiological saline for 4 hours and 24 hours followed by washing and drying as in Example 1. Thus, heparin having been fixed on the hollow fiber surface was quantified. As a result, it was confirmed that 12 mU/cm² and 10 mU/cm² of heparin had been fixed respectively after perfusing for 4 and 24 hours.

Comparative Example 1

The artificial lung $A_0$ obtained in Production Example 1 was heated to 50° C. with a hot air stream. Also, the solution (IV) obtained in Synthesis Example 4 was heated to 50° C. and then filled in the blood-contact face of the above-described artificial lung. An artificial lung (A4) having a coating film of the above-described solution (IV) on the blood-contact face was constructed as in Example 1. On the hollow fiber surface of this artificial lung (A4), 30 mU/cm² of heparin had been fixed. Then this artificial lung (A4) was perfused with physiological saline as in Example 1. Next, heparin having been fixed on the hollow fiber surface was quantified. As a result, it was confirmed that 0 mU/cm² of heparin had been fixed after perfusing for 4 hours. Namely, it was confirmed that all heparin fell off from the hollow fiber surface due to the contact of the blood-contact face of the artificial lung (A4) with sodium chloride in the physiological saline.

Comparative Example 2

The artificial lung $A_0$ obtained in Production Example 1 was heated to 50° C. with a hot air stream. Also, the solution (V) obtained in Synthesis Example 5 was heated to 50° C. and then filled in the blood-contact face of the above-described artificial lung. An artificial lung (A5) having a coating film of the above-described solution (V) on the blood-contact face was constructed as in Example 1. On the hollow fiber surface of this artificial lung (A5), a small amount (i.e., 4 mU/cm²) of heparin had been fixed. Then this artificial lung (A5) was perfused with physiological saline as in Example 1. Next, heparin having been fixed on the hollow fiber surface was quantified. As a result, it was confirmed that 3 mU/cm² and 3 mU/cm² of heparin had been fixed respectively after perfusing for 4 and 24 hours. Namely, it was confirmed that heparin scarcely fell off from the hollow fiber surface though heparin was fixed only in a small amount immediately after the formation of the coating film.

Comparative Example 3

The artificial lung $D_0$ obtained in Production Example 4 was heated to 50° C. with a hot air stream. Also, the solution (VI) obtained in Synthesis Example 6 was heated to 50° C. and then filled in the blood-contact face (the outer face of the hollow fiber) of the above-described artificial lung. An artificial lung (D1) having a coating film of the above-described solution (VI) on the blood-contact face was constructed as in Example 1. On the hollow fiber surface of this artificial lung (D1), 60 mU/cm² of heparin had been fixed. Then this artificial lung (D1) was perfused with physiological saline as in Example 1. Next, heparin having been fixed on the hollow fiber surface was quantified. As a result, it was confirmed that 7 mU/cm² and 1 mU/cm² of heparin had been fixed respectively after perfusing for 4 and 24 hours. Namely, it was confirmed that a considerably large portion of heparin fell off from the hollow fiber surface due to the contact of the blood-contact face of the artificial lung (D1) with sodium chloride in the physiological saline.

Comparative Example 4

The artificial lung ($A_0$) obtained in Production Example 1 was filled with fresh bovine blood the whole blood coagulation time of which had been adjusted to 200 sec. and then perfused with the blood at a flow rate of 1 L/min at 37° C. for 1 hour. After the completion of the perfusion, the artificial lung was thoroughly washed with physiological saline and observed. As a result, it was confirmed that a large amount of thrombi had adhered to the hollow fiber part of the artificial lung.

Because of having a coating film comprising a blood-compatible composition containing an ionic complex of specific ammonium salts having 4 aliphatic alkyl groups attached thereto with heparin, the artificial lung of membrane type according to the invention exhibits favorable antithrombotic properties and suffers from neither thrombus formation nor plasma leakage during using. Thus, it is useful as an artificial lung of membrane type usable over a long period of time.

While the invention has been described in detail and with reference to specific examples thereof, it will be apparent to one skilled in the art that various changes and modifications can be made therein without departing from the spirit and scope thereof.

What is claimed is:

1. A membrane artificial lung for performing gas exchange between blood and a gas via the membrane by flowing blood on a first surface of the membrane and flowing oxygen or an oxygen-containing gas on a second opposing surface of the membrane, said membrane comprising:

a hollow fiber membrane comprising poly-4-methylpentene-1, and having an oxygen permeation rate $Q(O_2)$ at 25° C. of from $5 \times 10^{-4}$ to $2 \times 10^{-3}$ ($cm^3$ (STP)/$cm^2$.sec.cmHg) and an ethanol flux of from 0.1 to 100 ml/min.$m^2$; and an ionic complex provided on said first surface of said membrane, said ionic complex comprising:

a first quaternary aliphatic alkylammonium salt having from 22 to 26 carbon atoms in total;

a second quaternary aliphatic alkylammonium salt having from 37 to 40 carbon atoms in total; and heparin or a heparin derivative.

2. The membrane artificial lung according to claim 1, said first quaternary aliphatic alkylammonium salt comprises 5 to 35 wt % of the weight of said first and said second quaternary aliphatic alkylammonium salts, and said second quaternary aliphatic alkylammonium salt comprises from 65 to 95 wt % of said weight of said first and said second quaternary aliphatic alkylammonium salts.

3. The membrane artificial lung according to claim 2, said first quaternary aliphatic alkylammonium salt comprises a dimethyldiododecylammonium salt and said second quaternary aliphatic alkylammonium salt comprises a dimethyldioctadecylammonium salt.

4. The membrane artificial lung according to claim 1, said first quaternary aliphatic alkylammonium salt comprises a dimethyldiododecylammonium salt and said second quaternary aliphatic alkylammonium salt comprises a dimethyldioctadecylammonium salt.

* * * * *